United States Patent [19]
Yasui et al.

[11] Patent Number: 5,733,244
[45] Date of Patent: Mar. 31, 1998

[54] DISTAL END PART OF ENDOSCOPE

[75] Inventors: Naoki Yasui; Hiroyuki Katsurada, both of Tokyo, Japan

[73] Assignee: Asahi Kogaku Kogyo Kabushiki Kaisha, Tokyo, Japan

[21] Appl. No.: 611,870

[22] Filed: Mar. 6, 1996

[30]     Foreign Application Priority Data

Mar. 13, 1995  [JP]  Japan ..................... 7-52160
Dec. 7, 1995   [JP]  Japan ..................... 7-318786

[51] Int. Cl.$^6$ .................................. A61B 1/04
[52] U.S. Cl. ................. 600/127; 600/121; 600/129
[58] Field of Search ................. 600/121, 123, 600/125, 127, 129, 153, 156, 157, 158, 203, 187, 205, 188

[56]         References Cited

U.S. PATENT DOCUMENTS

| | | |
|---|---|---|
| 4,211,214 | 7/1980 | Chikashige . |
| 4,971,035 | 11/1990 | Ito . |
| 5,050,585 | 9/1991 | Takahashi . |
| 5,193,263 | 3/1993 | Takahashi . |
| 5,305,736 | 4/1994 | Ito . |
| 5,325,847 | 7/1994 | Matsuno . |

FOREIGN PATENT DOCUMENTS

6-015529   5/1985   Japan .

*Primary Examiner*—Beverly M. Flanagan
*Attorney, Agent, or Firm*—Greenblum & Bernstein, P.L.C.

[57]            ABSTRACT

A distal end part of an endoscope including an end cap provided with a nozzle for spouting a fluid in a predetermined direction. The end cap is detachable with respect to a distal end block which is provided at the distal end of an insert part of the endoscope. Engagement portions are provided on the end cap and the distal end block to regulate the condition in which the end cap is fitted to the distal end block. The engagement portion of the end cap and the engagement portion of the distal end block are formed such that, among different models of endoscopes in which the distal end blocks have approximately the same outer diameter, the engagement portion of the end cap off one model cannot be engaged with the engagement portion of the distal end block of another model.

18 Claims, 7 Drawing Sheets

# DISTAL END PART OF ENDOSCOPE

BACKGROUND OF THE INVENTION

The present disclosure relates to subject matter contained in Japanese Patent Application No. 7-52160 (filed on Mar. 13, 1995) and Japanese Patent Application No. 7-318786 (filed on Dec. 7, 1995), which are expressly incorporated herein by reference in their entireties.

1. Field of the Invention

The present invention relates to a distal end part of an endoscope in which a nozzle is formed on an end cap which is detachable with respect to a distal end block of the endoscope.

2. Description of the Related Art

In general, the end cap of an endoscope is formed of an elastic material, such as rubber, so as to be detachably fitted onto the distal end block of the endoscope.

The distal end part of an endoscope is provided with a nozzle for spraying the surface of a viewing window with a fluid, e.g. water or air, and for washing filth such as mucus or blood away from the surface of an object of endoscopy. In earlier models, the nozzle was provided on the distal end block; earlier models, in the majority of more recent models of endoscopes, the nozzle is formed on the end cap in view of cleaning of the fluid conduits.

The end cap, which is provided with a nozzle, and the distal end block are provided with projecting and recessed engagement portions, respectively, which engaged with each other when the end cap is fitted to the distal end block, so that the nozzle is set in the correct position with respect to the distal end block.

However, there are many models of endoscopes, and more than a few models in which the distal end blocks have almost the same outer diameter. Therefore, in a case where there are different models of endoscopes which are almost equal in the outer diameter of their distal end blocks, an end cap may be mistakenly fitted to the distal end block of the wrong endoscope.

If such a mistake is made, a fluid is not spouted in a predetermined direction because the nozzle position differs among different models. This situation causes an interference with the endoscopic observation. Further, an abnormal condition such as "eclipse" may occur in the illumination and the field of view.

SUMMARY OF THE INVENTION

An object of the present invention is to provide a distal end part of an endoscope which is designed so that the end cap is prevented from being mistakenly fitted to the distal end block of the wrong endoscope in a case where there are different models of endoscopes in which the distal end blocks have approximately the same outer diameter.

Other objects and advantages of the present invention will become apparent from the following detailed description of illustrated embodiments of the invention.

According to the present invention, there is provided a distal end part of an endoscope which includes an end cap provided with a nozzle for spouting a fluid in a predetermined direction. The end cap is detachable with respect to a distal end block which is provided at the distal end of an insert part of the endoscope. The distal end part further includes engagement devices provided on the end cap and the distal end block to regulate the condition in which the end cap is fitted to the distal end block. The engagement devices are recessed and projecting portions which are engageable with each other. The engagement device of the end cap and the engagement device of the distal end block are formed such that, among different models of endoscopes in which the distal end blocks have approximately the same outer diameter, the engagement device of the end cap of one model cannot be engaged with the engagement device of the distal end block of another model.

BRIEF DESCRIPTION OF THE DRAWINGS

The present invention may be more fully understood from the description of preferred embodiments of the invention set forth below, together with the accompanying drawings, in which.

DESCRIPTION OF THE EMBODIMENTS

Embodiments of the present invention will be described below with reference to the accompanying drawings.

Figure 1:
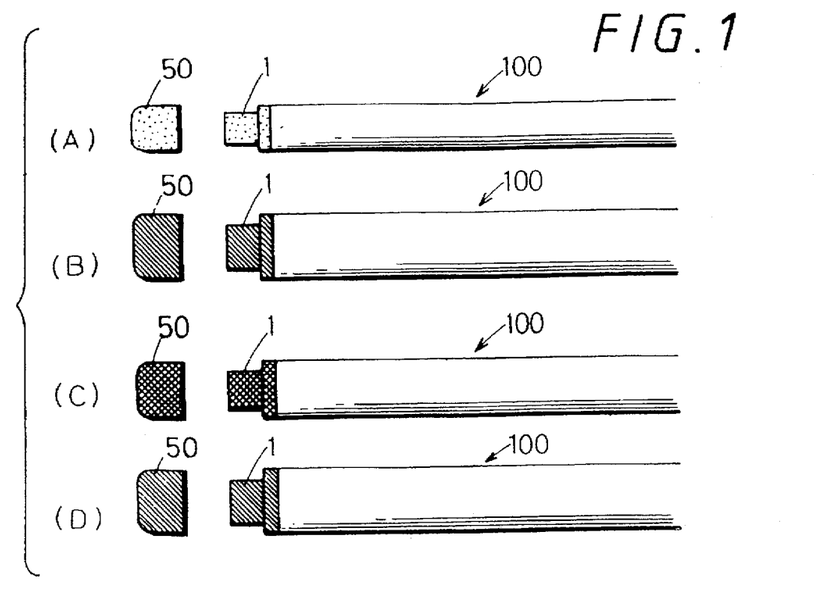
FIG. 1 is a side view showing various models A through D of end-viewing endoscopes with their insert part distal ends placed side by side.

FIG. 1 shows insert parts 100 of four different models A to D of end-viewing endoscopes. Each insert part 100 has a distal end block 1 connected to the distal end thereof.

Each distal end block 1 is provided with a detachable end cap 50 made of an elastic material, e.g. a rubber material. In FIG. 1, the insert parts 100 are shown with the end caps 50 detached therefrom.

Among the four models A to D, the models A, B and C are different from each other in the outer diameter of the distal end blocks 1. Therefore, there is no possibility that any of the end caps 50 for the models A, B and C will be fitted to the distal end block 1 of a wrong endoscope among the three models. However, the outer diameter of the distal end block 1 of the model D is approximately the same as that of the distal end block 1 of the model B.

Figure 2:
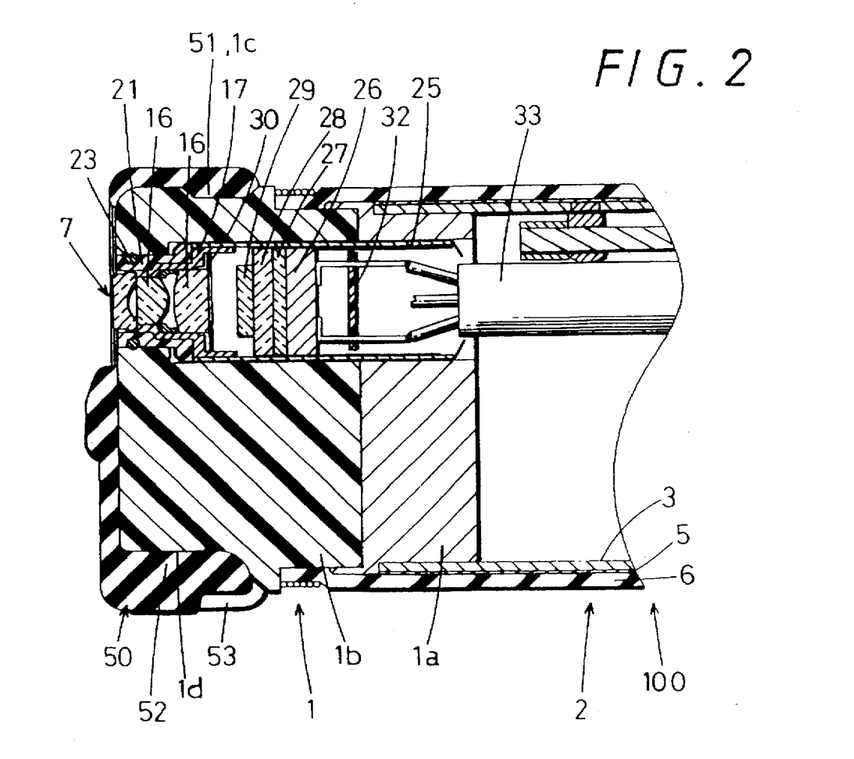
FIG. 2 is a sectional side view of a model B of an end-viewing endoscope arranged according to one embodiment of the present invention.
Figure 3:
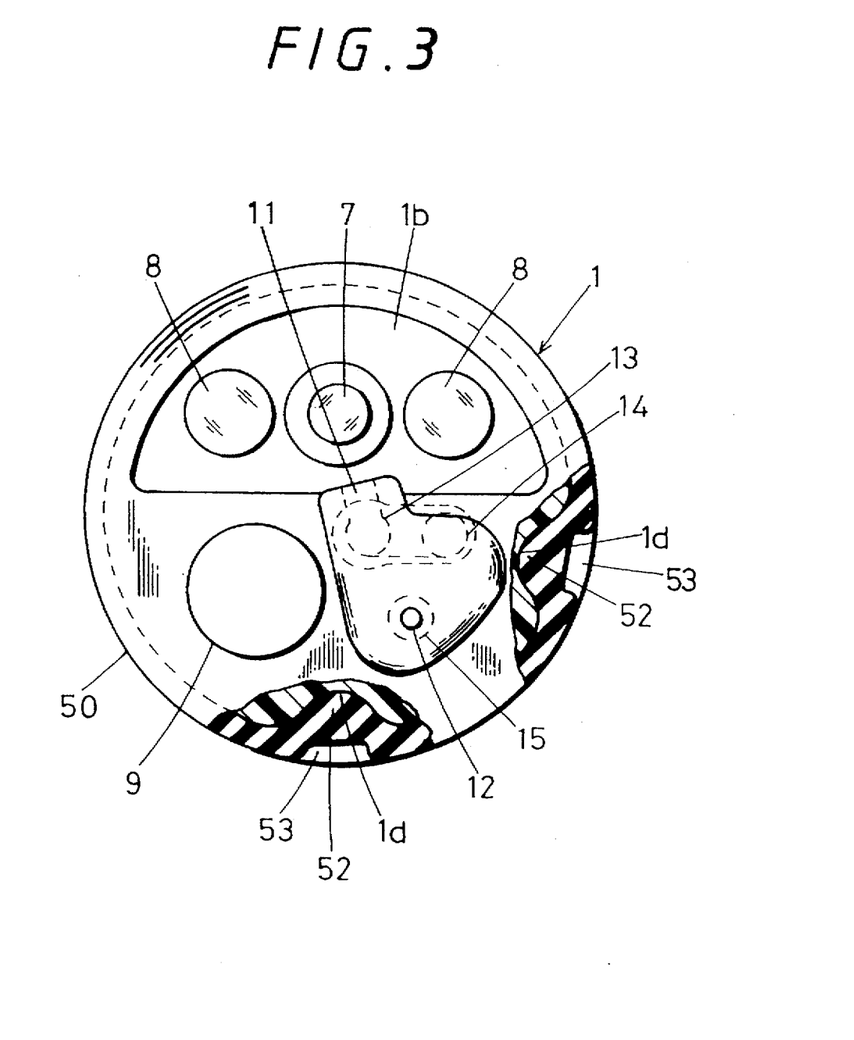
FIG. 3 is a front view of the model B of an end-viewing endoscope arranged according to one embodiment of the present invention.

FIG. 2 is a sectional side view of the distal end portion of the insert part 100 of the model B, and FIG. 3 is a front view of it. The insert part 100 is formed from an elongated flexible tube. The distal end block 1 is connected to the distal end portion of a bendable portion 2 which is provided at the distal end of the insert part 100 such that the bendable portion 2 is bendable by remote control.

The bendable portion 2 is formed by pivotally connecting together a large number of joint rings 3 by rivets, and covering the outer periphery of the train of joint rings 3 with a braid tube 5. Further, the braid tube 5 is sheathed with a rubber tube 6, and the end portion of the rubber tube 6 is tightly tied and bonded to the outer peripheral surface of the distal end block 1.

The distal end block 1 is formed from a metal block portion 1a and a plastic block portion 1b. The metal block portion 1a is made of stainless steel and connected to the distal end of the bendable portion 2 such that the metal block portion 1a is not exposed to the outside. The plastic block portion 1b is rigidly secured to the forward end of the metal block portion 1a, and the forward end portion of the plastic block portion 1b is exposed to the outside. It should be noted that the term "forward" used herein is employed to mean the distal end side of the endoscope insert part 100, and the term "rear" used herein is employed to mean the proximal end side of the endoscope insert part 100.

The endoscope in this embodiment is an end-viewing endoscope designed to view forwardly in the axial direction of the endoscope (the same direction as the axis of the distal end block 1). Accordingly, as shown in FIG. 3, a viewing window 7, illuminating windows 8 and a forceps channel outlet 9 are provided in the distal end surface of the distal end block 1.

The end cap 50 is formed of an electrically insulating and elastic material, e.g. polyurethane rubber. The end cap 50 is fitted onto the outer peripheral surface or the distal end block 1 from the distal end of the block 1.

The end cap 50 is provided with an air-water nozzle 11 which opens toward the surface of the viewing window 7, and a jet nozzle 12 which opens forwardly toward an object of endoscopy.

An air supply conduit 13 and a water supply conduit 14 are formed in the distal end block 1 so as to communicate with the air-water nozzle 11. A sub-water supply conduit 15 is formed in the distal end block 1 so as to communicate with the jet nozzle 12. The conduits 13, 14 and 15 are connected to respective tubes (not shown) which are inserted in the insert part 100.

As shown in FIG. 2, an objective optical system 16 is disposed inside the viewing window 7. The objective optical system 16 is rigidly secured in a metallic lens frame 17. An insulating ring 21, which is made of an electrically insulating plastic material, is bonded to the outer peripheral portion of the front portion of the lens frame 17.

The outer peripheral surface of the insulating ring 21 is fitted to the wall of a bore formed in the plastic block portion 1b of the distal end block 1. An O-ring 23 for sealing is disposed in the area of fit between the insulating ring 21 and the plastic block portion 1b.

A metallic shield pipe 25 is fitted and bonded to the outer peripheral portion of the rear portion of the lens frame 17. A solid-state imaging device 26, e.g. a charge-coupled device (CCD), is secured in the shield pipe 25 with the image-receiving surface facing forwardly.

In front of the solid-state imaging device 26, a transparent cover glass 27 is disposed in close contact with the image-receiving surface of the solid-state imaging device 26, and a low-pass filter 28 and a YAG laser light cutoff filter 29 are disposed in front of the cover glass 27.

An observation light image is formed on the image-receiving surface of the solid-state imaging device 26 by the objective optical system 16 through the transparent members 27, 28 and 29. A mask 30 intercepts undesired light at the edges of the optical path.

Electronic parts for processing signals input to and output from the solid-state imaging device 26 are mounted on a wiring board 32. The wiring board 32 is disposed in the shield pipe 25, and a signal cable 33 extends rearwardly from the wiring board 32.

It should be noted that the present invention is also applicable to an endoscope which employs an optical image transmitting device using an image guide fiber bundle in place off the electronic image transmitting device using the solid-state imaging device 26. The present invention may also be applied to a rigid endoscope.

As shown in FIG. 2, the inner peripheral surface of the rear portion of the end cap 50 is provided with a retaining projection 51 which projects inwardly so that, when the end cap 50 is fitted to the distal end block 1, the projection 51 is engaged with a circumferential groove 1c formed in the outer peripheral surface of the distal end block 1, thereby preventing the end cap 50 from coming off. It should be noted that the term "rear" used herein is also employed to mean the proximal end side of the endoscope insert part 100.

As shown in FIG. 3, the end cap 50 further has engagement projections 52 for positioning at two positions, respectively. More specifically, one engagement projection 52 projects inwardly from the lower end portion of the end cap 50, and the other engagement projection 52 projects inwardly from the inner peripheral surface of the left side portion of the end cap 50 so that, when the end cap 50 is fitted to the distal end block 1, the engagement projections 52 are engaged with respective grooves 1d which are formed in the outer peripheral surface of the distal end block 1 to extend straight in the axial direction. The grooves 1d are deeper than the circumferential groove 1c, and the lengths (axial lengths) of the engagement projections 52 are the same as or shorter than those of the respective grooves 1d.

Accordingly, the end cap 50 is fitted to the distal end block 1 only in the position where the engagement projections 52 are engaged with the grooves 1d. Thus, when the end cap 50 is fitted to the distal end block 1, the two engagement projections 52 are engaged with the respective grooves 1d, thereby positioning the end cap 50 with respect to the distal end block 1 in the direction of rotation.

Further, there is only one position where the two engagement projections 52 are engaged with the respective grooves 1d because the engagement projections 52 are not in 180 degree symmetric relation to each other in the direction of rotation. Therefore, there is no possibility of the end cap 50 being fitted to the distal end block 1 in a wrong position in the direction of rotation.

The outer peripheral surface of the end cap 50 is provided with marking recesses (index marks) 53 at respective positions corresponding to the two engagement projections 52, so that it is possible to judge whether or not the end cap 50 is the one that should be fitted to the distal end block 1 in question by comparing the positions of the recesses 53 with the positions of the grooves 1d of the distal end block 1. It should be noted that all ridges of the end cap 50 are smoothly rounded so that the end cap 50 will not injure the mucous membrane in the patient's body cavity.

When the end cap 50 is to be fitted to the distal end block 1, the rear end of the end cap 50 is pressed against the forward end of the distal end block 1 so as to expand by elastic deformation, and thus the retaining projection 51, which is formed on the rear end inner surface of the end cap 50, is forced to move along the outer peripheral surface of the distal end block 1. In this way, the end cap 50 is forced to fit on the distal end block 1 of the endoscope. In this ease, however, the engagement projections 52 must be aligned with respect to the grooves 1d in advance.

Consequently, the distal end block 1 enters the end cap 50, and as the retaining projection 51 on the inner surface of the end cap 50 fits in the circumferential groove 1c in the outer peripheral surface of the distal end block 1, the end cap 50 is restored to the previous shape as shown in FIG. 2 by its own elasticity. Thus, the end cap 50 is locked so as not to come off from the distal end block 1.

At this time, the positioning engagement projections 52 are fitted in the grooves 1d. Therefore, the end cap 50 is positioned with respect to the distal end block 1 in the direction of rotation. Accordingly, the air supply conduit 13 and the water supply conduit 14 are communicated with the air-water nozzle 11 without positional displacement, and the sub-water supply conduit 15 is also communicated with the jet nozzle 12 without positional displacement.

Figure 4:
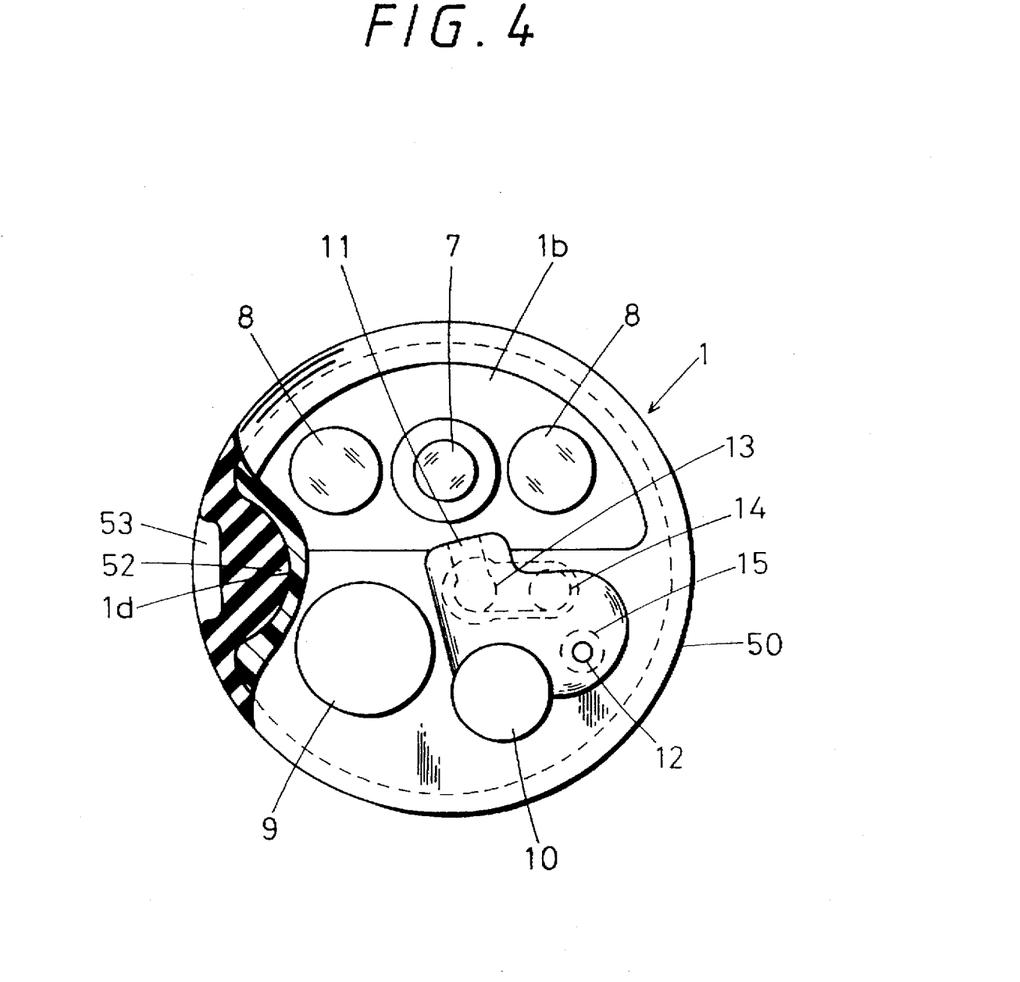
FIG. 4 is a front view of a model D of an end-viewing endoscope arranged according to one embodiment of the present invention.
Figure 5:
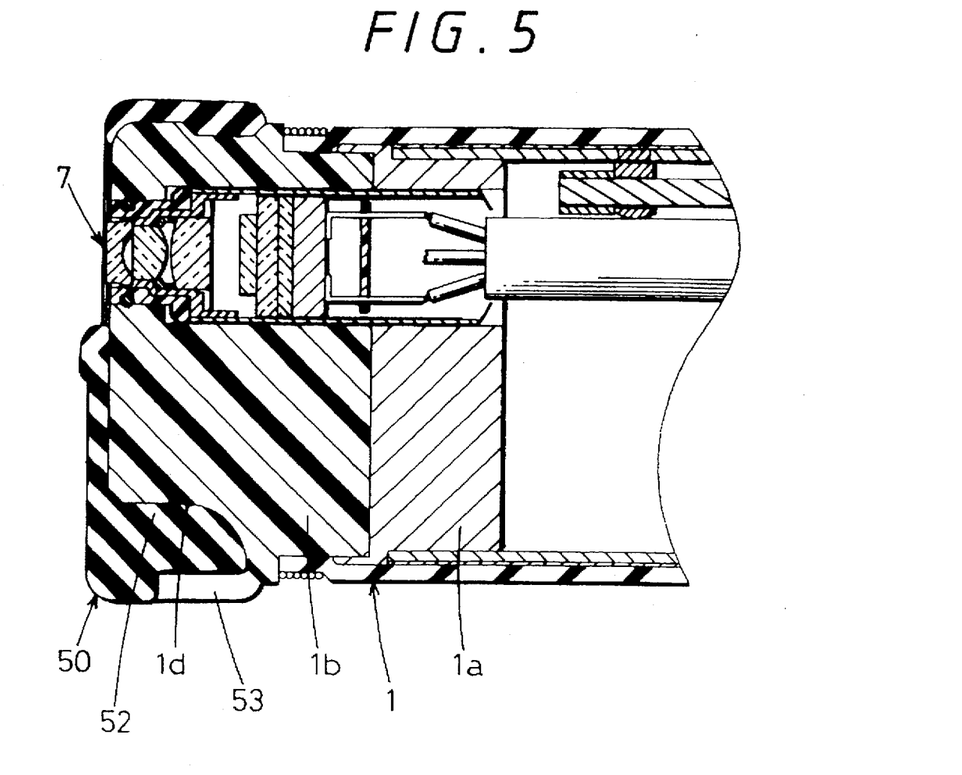
FIG. 5 is a sectional side view of the model D of an end-viewing endoscope arranged according to one embodiment of the present invention.

FIGS. 4 and 5 show the distal end portion of the insert part 100 of the model D in which the outer diameter of the distal end block 1 is approximately the same as that of the distal end block 1 of the above-described model B. In the model D, two forceps channel outlets 9 and 10 are provided. Accordingly, the positions of the air supply conduit 13, the water supply conduit 14, the sub-water supply conduit 15 and so forth are displaced relative to those in the model B. The other portions of the model D, such as the optical system and other constituent elements, are the same as those of the model B.

The end cap 50 of the model D is provided with only one engagement projection 52 which is engageable with a groove 1d provided on the distal end block 1. The engagement projection 52 is provided on the right side of the end cap 50. However, the engagement projection 52 is much larger in size than the engagement projections 52 of the end cap 50 of the model B. A marking recess 53 is formed in the outer surface of the engagement projection 52. The marking recess 53 of the model D (FIGS. 5 and 6) is larger than the marking recesses 53 of the model B (FIGS. 2 and 3).

Accordingly, the end cap 50 of the model D cannot be fitted to the distal end block 1 of the model B because the engagement projection 52 cannot be engaged with either of the grooves 1d formed on the distal end block 1 of the model B. Conversely, the end cap 50 of the model. B cannot be fitted to the distal end block 1 of the model D because neither of the engagement projections 52 can be engaged with the groove 1d formed on the distal end block 1 of the model D.

Figure 6:
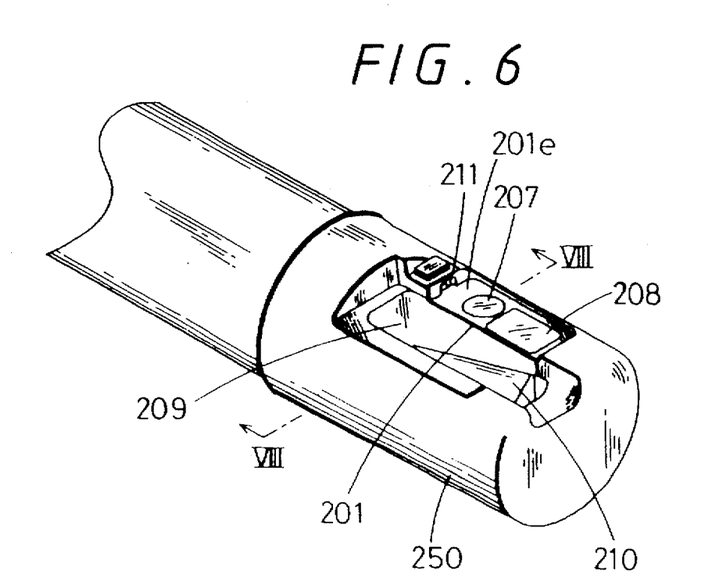
FIG. 6 is a perspective view of a model X of a side-viewing endoscope arranged according to one embodiment of the present invention.
Figure 7:
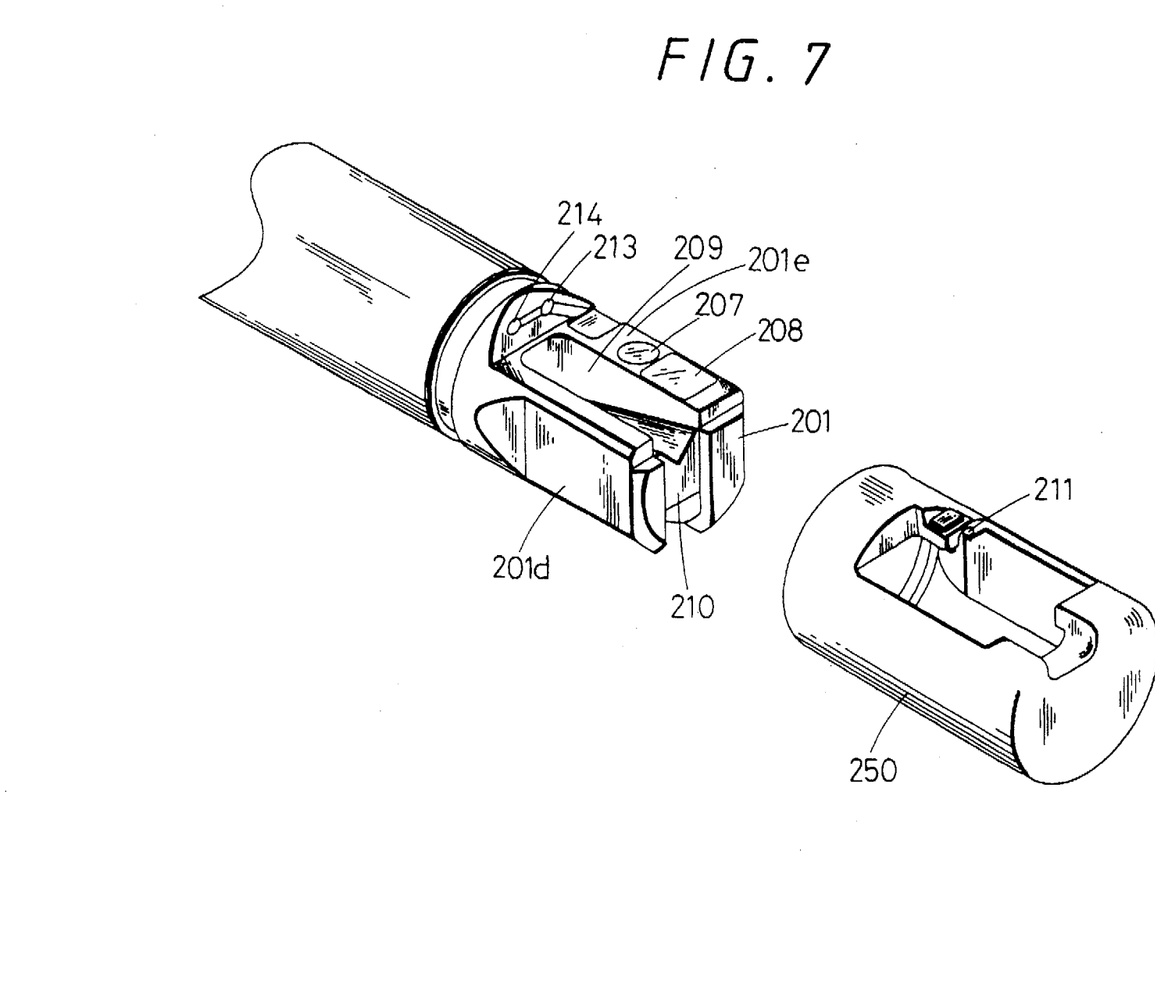
FIG. 7 is a perspective view showing the model X of a side-viewing endoscope with an end cap detached therefrom.

FIGS. 6 and 7 show the insert part distal end portion of a model X of side-viewing endoscope arranged according to one embodiment of the present invention. FIG. 6 shows an end cap 250 which is made of an elastic plastic material and detachable with respect to a metallic distal end block 201. In FIG. 6, the distal end block 201 is fitted with the end cap 250. FIG. 7 shows the distal end block 201 with the end cap 250 detached therefrom.

The distal end block 201 is formed from a cylindrical stock. One side of the cylindrical stock is cut into a flat surface to form a flat portion 201e. A viewing window 207 and an illuminating window 208 are disposed side by side on the flat portion 201e. The two windows 207 and 208 face sidewardly so that it is possible to view sidewardly of the distal end block 201. A large opening is provided side by side with the windows 207 and 208 to form a forceps channel outlet 209. A remote-controlled forceps guide member 210 is disposed in the forceps channel outlet 209.

An air-water nozzle 211 is formed on the end cap 250 so as to open toward the viewing window 207. An air supply conduit 213 and a water supply conduit 214 are formed in the distal end block 201 so that, when the end cap 250 is fitted to the distal end block 201, the two conduits 213 and 214 are communicated with the air-water nozzle 211.

The distal end block 201 has planar cut portions 201d formed on both sides which extend at right angles to the fiat portion 201e, on which the viewing window 207 and the illuminating window 208 are disposed.

Figure 8:
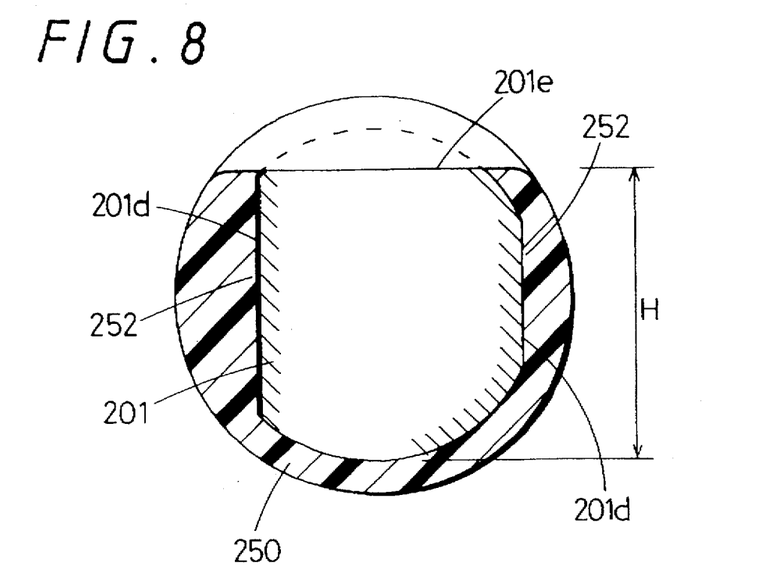
FIG. 8 is a schematic sectional front view (VIII—VIII in FIG. 6) of the model X of a side-viewing endoscope.

The end cap 250 has a large opening provided in a side thereof which is to lie over the flat portion 201e. As shown in FIG. 8, which is a schematic sectional view taken along the line VIII—VIII in FIG. 6, the other portion of the end cap 250 is formed so that the whole inner peripheral surface thereof comes into contact with the outer peripheral surface of the distal end block 201. In this state, the flat portion 201e is exposed.

Accordingly, flat portions 252 which are formed on the inner peripheral surfaces of the left and right sides of the end cap 250 wholly come into contact with the planar cut portions 201d formed on the distal end block 201, and thus the end cap 250 is fitted to the distal end block 201 so as not to rotate.

Figure 9:
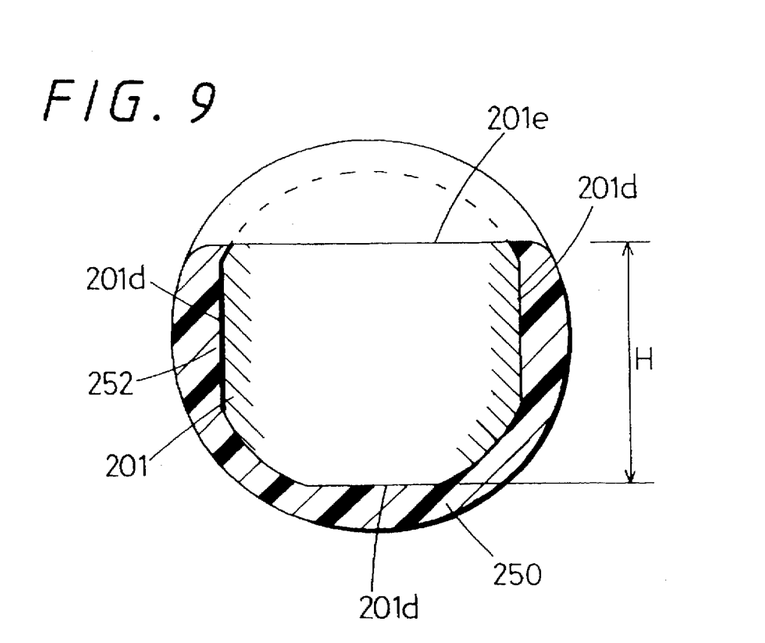
FIG. 9 is a schematic sectional front view of a model Y of a side-viewing endoscope arranged according to one embodiment of the present invention.
Figure 10:
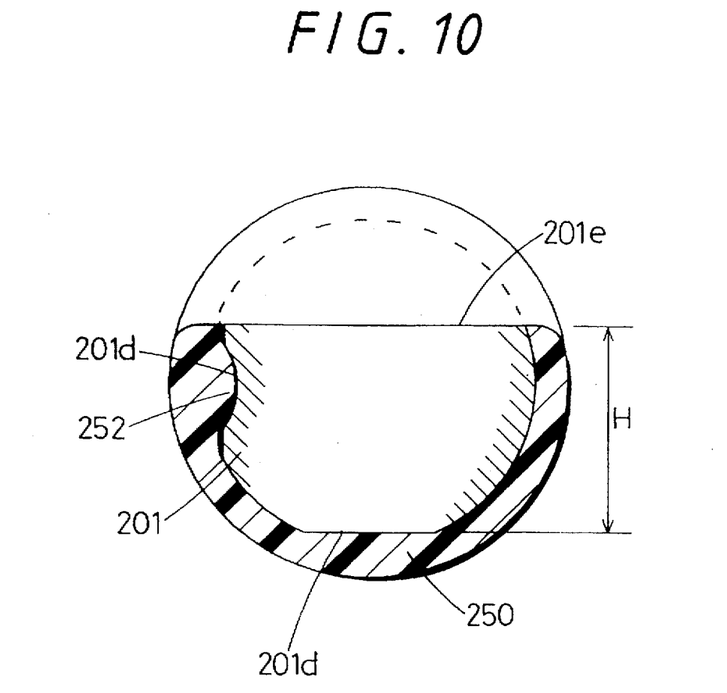
FIG. 10 is a schematic sectional front view of a model Z of a side-viewing endoscope arranged according to one embodiment off the present invention.

FIGS. 9 and 10 respectively show models Y and Z of side-viewing endoscopes arranged according to one embodiment of the present invention. These figures show only cross-sections of the two models Y and Z which correspond to the sectional view of FIG. 8. In both the models Y and Z, the outer diameter of the distal end block 201 is approximately the same as that of the model X. However, the models X, Y and Z differ from each other in the height H to the flat portion 201e, the structure of the air-water nozzle 211, etc. Therefore, the models X, Y and Z cannot use each other's end cap 250.

Thus, by varying the depth, shape or number of cut portions 201d formed on the sides of the distal end block 201 of the models Y and Z from those of the model X, it is possible to prevent each particular end cap 250 from being fitted to the distal end block 201 of a wrong endoscope among different models. For example, the model Y is provided with three cut portions 201d. In the model Z, one cut portion 201d is partially concaved.

It should be noted that the present invention is not necessarily limited to the above-described embodiments. It is essential only that at least one of the position, size, number, etc. of engagement portions provided on the end cap 50 (250) and the distal end block 1 (201) differ among different models in which distal end blocks have approximately the same outer diameter so that the engagement portions of the end cap 50 (250) of one model cannot be engaged with the engagement portions of the distal end block 1 (201) of another model.

According to the present invention, different models of endoscopes in which distal end blocks have approximately the same outer diameter are arranged so that the engagement portions of the end cap of one model cannot be engaged with the engagement portions of the distal end block of another model. Therefore, there is no possibility that each particular end cap will be fitted to the distal end block of a wrong endoscope among different models in which the outer diameters of the distal end blocks are almost the same.

Further, by forming an index mark on the outer peripheral portion of each end cap at a position corresponding to each engagement portion, it is possible to recognize the distal end block of a particular model to which the end cap should be fitted. In a model which is provided with a plurality of engagement portions, the engagement portions are formed at respective positions which are not symmetric in the direction of rotation, thereby making it possible to prevent the end cap from being fitted to the distal end block in a wrong position in the direction of rotation.

While the invention has been described by reference to specific embodiments chosen for purposes of illustration, it should be apparent that numerous modifications could be made thereto by those skilled in the art without departing from the basic concept and scope of the invention.

I claim:

1. A system of different models of endoscopes, each endoscope having a distal end part, each distal end part comprising:

an end cap provided with a nozzle for spouting a fluid in a predetermined direction, said end cap being detachable with respect to a distal end block which is provided at a distal end of an insert part of an endoscope; and engagement means provided on said end cap and said distal end block to regulate a condition in which said end cap is fitted to said distal end block, said engagement means including mating portions which are engageable with each other, said mating portions also positioning the end cap with respect to said distal end block in a direction of rotation, said engagement means provided on said end cap and said engagement means provided on said distal end block being formed such that, among said different models of endoscopes in said system in which distal end blocks have approximately the same outer diameter, said engagement means provided on said end cap of one model cannot be engaged with said engagement means provided on said distal end block of another model.

2. The system according to claim 1, wherein said end cap comprises an elastic material, so that said end cap is fitted on an outer peripheral surface of said distal end block.

3. The system according to claim 2, wherein said mating portions comprise recessed and projecting portions.

4. The system according to claim 3, wherein an outer peripheral surface of said distal end block is provided with a circumferential groove, and an inner peripheral surface of said end cap is provided with a retaining projection which is engageable with said circumferential groove to prevent said end cap from coming off from said distal end block.

5. The system according to claim 4, wherein the outer peripheral surface of said distal end block is provided with at least one axial straight groove, and said end cap is provided with at least one positioning projection which is engageable with said axial straight groove.

6. The system according to claim 5, wherein, when said end cap is to be fitted to said distal end block, said end cap is elastically deformed by being forced to expand by said distal end block, and after said end cap has been fitted to said distal end block, said end cap is restored to a previous shape by its own elasticity.

7. The system according to claim 5, wherein at least one of position, size and number of said axial straight groove and said positioning projection differs among said different models of endoscopes.

8. The system according to claim 7, wherein, in a model of endoscope which is provided with a plurality of combinations of said axial straight grooves and said positioning projections, said grooves and projections are formed at respective positions which are asymmetric in a direction of rotation.

9. The system according to claim 5, wherein said endoscope is an end-viewing endoscope designed to view forwardly of said distal end block.

10. The system according to claim 3, wherein said distal end block has a non-circular cross-sectional configuration.

11. The system according to claim 10, wherein a portion of said distal end block which has a non-circular cross-sectional configuration varies in shape among said different models of endoscopes.

12. The system according to claim 10, wherein said endoscope is a side-viewing endoscope designed to view sidewardly of said distal end block.

13. The system according to claim 12, wherein one of said mating portions comprises at least a planar cut portion formed on said distal end block, and the other of said mating portions comprises at least a flat portion formed on an inner peripheral surface of said end cap.

14. The system according to claim 12, wherein said recessed portion includes at least one recess on said distal end block, and said projecting portion includes at least one projection on an inner peripheral surface of said end cap.

15. The system according to claim 1, wherein at least one of position, size and number of said engagement means differs among said different models of endoscopes.

16. A system of different models of endoscopes, each endoscope having a distal end part, each distal end part comprising:

an end cap provided with a nozzle for spouting a fluid in a predetermined direction, said end cap being detachable with respect to a distal end block which is provided at a distal end of an insert part of an endoscope; and engagement means provided on said end cap and said distal end block to regulate a condition in which said end cap is fitted to said distal end block, said engagement means including mating portions which are engageable with each other, said engagement means provided on said end cap and said engagement means provided on said distal end block being formed such that, among said different models of endoscopes in which distal end blocks have approximately the same outer diameter, said engagement means provided on said end cap of one model cannot be engaged with said engagement means provided on said distal end block of another model, and an outer peripheral surface of said end cap being provided with an index mark at a position corresponding to said engagement means.

17. The system according to claim 16, wherein said index mark is formed from a recess.

18. A system of different models of endoscopes, each endoscope having a distal end part, each distal end part comprising:

an end cap provided with a nozzle for spouting a fluid in a predetermined direction, said end cap being detachable with respect to a distal end block which is provided at a distal end of an insert part of an endoscope; and engagement means provided on said end cap and said distal end block to regulate a condition in which said end cap is fitted to said distal end block, said engagement means including mating portions which are engageable with each other, said engagement means provided on said end cap and said engagement means provided on said distal end block being formed such that, among said different models of endoscopes in which distal end blocks have approximately the same outer diameter, said engagement means provided on said end cap of one model cannot be engaged with said engagement means provided on said distal end block of another model, wherein an outer peripheral surface of said distal end block is provided with at least one axial straight groove extending to a distal end portion of said distal end block, and said end cap is provided with at least one positioning projection on an inner peripheral surface which is engageable with said axial straight groove, said positioning projection extending to an entrance of said inner peripheral surface.

* * * * *

UNITED STATES PATENT AND TRADEMARK OFFICE
CERTIFICATE OF CORRECTION

PATENT NO. : 5,733,244
DATED : March 31, 1998
INVENTOR(S) : Naoki YASUI et al.

It is certified that error appears in the above-identified patent and that said Letters Patent is hereby corrected as shown below:

On the cover page of the printed patent, paragraph [56] References Cited, U.S. PATENT DOCUMENTS, the following should be inserted:

```
---   4,646,722   3/1987    Silverstein et al.
      4,794,911   1/1989    Okada
      4,881,810   11/1989   Hasegawa
      5,193,525   3/1993    Silverstein et al.
      5,518,501   5/1996    Oneda et al.---
```

Also insert:    FOREIGN PATENT DOCUMENTS
```
                6-14865     1/1994    Japan
                56-4348     3/1994    Japan
                58-87442    5/1995    Japan
```

Signed and Sealed this

Twelfth Day of January, 1999

Attest:

Attesting Officer    *Acting Commissioner of Patents and Trademarks*